United States Patent [19]

Wagner

[11] Patent Number: 4,757,075

[45] Date of Patent: Jul. 12, 1988

[54] TETRAZOLYLQUINAZOLINONES AS ANTI-HYPERURICEMIC AGENTS

[75] Inventor: Steven R. Wagner, Indianapolis, Ind.

[73] Assignee: Merrell Dow Pharmaceuticals Inc., Cincinnati, Ohio

[21] Appl. No.: 918,405

[22] Filed: Oct. 14, 1986

[51] Int. Cl.[4] .............................................. A61K 31/505
[52] U.S. Cl. ...................................................... 514/259
[58] Field of Search ......................................... 514/259

[56] References Cited

U.S. PATENT DOCUMENTS 4,419,357 12/1983 Peet et al. ............................ 514/259
4,451,467 5/1984 Ishikawa et al. ..................... 514/259
4,599,336 7/1986 Carson et al. ........................ 514/259

OTHER PUBLICATIONS

Conn's Current Therapy, pp. 431–433, 1984.
Conn's Current Therapy, pp. 454–457, 1986.

Primary Examiner—Albert T. Meyers
Assistant Examiner—John M. Kilcoyne
Attorney, Agent, or Firm—John J. Kolano

[57] ABSTRACT

A method of reducing serum levels of uric acid which comprises administration of 3-(1H-tetrazol-5-yl)-4(3H)-quinazolinone or its pharmaceutically acceptable salts is described herein.

5 Claims, No Drawings

TETRAZOLYLQUINAZOLINONES AS ANTI-HYPERURICEMIC AGENTS

BACKGROUND OF THE INVENTION

Hyperuricemia, or an excess of uric acid in the blood, can lead to attacks of gout and may be a risk factor for the development of cardiovascular disease, carbohydrate intolerance, and urate-induced nephropathy. Thus, methods of lowering levels of uric acid in the blood would be useful.

3-(1H-Tetrazol-5-yl)-4(3H)-quinazolinones have been described in U.S. Pat. No. 4,419,357 as useful as antiallergic agents but the patent gives no indication that the compounds would have any effect on uric acid levels in the blood.

DETAILED DESCRIPTION OF THE INVENTION

It has now been found that 3-(1H-tetrazol-5-yl)-4(3H)-quinazolinone and its salts, when administered orally to humans, are useful in reducing levels of uric acid in the blood. Thus, the present invention is directed to a method of reducing levels of uric acid in the blood and, more particularly, of treating hyperuricemia by the administration of an effective amount of 3-(1H-tetrazol-5-yl)-4(3H)-quinazolinone or a pharmaceutically acceptable salt thereof.

More particularly, the method as described herein relates to the use of various equivalent forms of 3-(1H-tetrazol-5-yl)-4(3H)-quinazolinone. That is, it encompasses the use of the compound itself and its hydrates and also the pharmaceutically acceptable salts of the compound and hydrates of the salts. More specifically, the compound is an acid and all the various forms referred to above are considered as equivalent to the acid because, when administered orally, they would all give the free acid in the stomach. The term "pharmaceutically-acceptable salt" as used herein is intended to include non-toxic cationic salts such as the alkali metal salts, e.g., sodium and potassium; alkaline earth metal salts such as calcium, magnesium and barium; salts with ammonia; and salts with organic bases, e.g., amines such as triethylamine, n-propylamine and tri-n-butylamine. The alkali metal salts and, particularly the sodium salt, are preferred.

Specifically, 3-(1H-tetrazol-5-yl)-4(3H)-quinazolinone can be converted to the basic pharmaceutically acceptable salts by reaction of the tetrazole with a substantially equimolar amount of the appropriate base in an aqueous solution or any suitable organic solvent such as methanol or ethanol. The salts are recovered by standard methods such as filtration if they are insoluble in the original medium, or if they are soluble in that medium, the salt is precipitated by evaporation of the solvent or by addition of a non-solvent for the salt. A detailed description of the preparation of some salts is provided by U.S. Pat. No. 4,419,357 referred to earlier.

To bring about a reduction of uric acid levels in the blood, the tetrazolylquinazolinone of this invention or its pharmaceutically acceptable salts is preferably administered in doses of 50 mg to 500 mg given orally 4 times daily, although the indicated doses could be administered less frequently, for example, twice daily. The tetrazolylquinazolinone or its salts can be administered in the standard oral dosage forms such as capsules or tablets and any such dosage forms are prepared by standard procedures as described in *Remington's Pharmaceutical Sciences*, Mack Publishing Company, Easton, Pa.

As an example, tablets can be prepared by direct compression through a slugging process with the final composition of individual tablets being as follows:

| Ingredient | mg/tablet |
|---|---|
| Sodium salt of 3-(1H—tetrazol-5-yl)-4(3H)—quinazolinone | 500.0 |
| Magnesium stearate, NF | 4.0 |
| Microcrystalline cellulose, NF | q.s. |
| Total weight | 800.0 |

The active ingredient used in the formulation may contain some associated water, but the theoretical amount of active ingredient present in the tablet is expressed on an anhydrous basis. Thus, the actual weight of drug substance used is adjusted for the water content. The microcrystalline cellulose NF is added in a quantity sufficient to bring the tablet to the theoretical total weight and the exact amount used will vary depending on the amount of water present in the active ingredient.

The effectiveness of the compound in reducing uric acid levels in the blood was demonstrated by the following procedure. Four groups of subjects were used, each consisting of six normal individuals. Each group consisted of four subjects who received the active substance 4 times daily at 4 hour intervals for 5 days; two additional subjects in each group received placebo. Capsules containing the sodium salt of 3-(1H-tetrazol-5-yl)-4(3H)-quinazolinone were administered orally at doses of 200, 300, 400, and 500 mg with each group referred to above receiving the compound at one specific dose level. Serum uric acid was measured and the results are summarized in Table I below.

TABLE I

| | SERUM URIC ACID CONCENTRATION (MEAN MG/DL ± S.E.) | | | | |
|---|---|---|---|---|---|
| | | Treatment | | | |
| | Placebo | 200 mg | 300 mg | 400 mg | 500 mg |
| No. of Patients | 8 | 4 | 4 | 4 | 4 |
| Screening | 5.54 ± .43 | 6.42 ± .79 | 5.10 ± .39 | 5.18 ± .55 | 6.20 ± .23 |
| Day 1 | 5.46 ± .39 | 6.28 ± .56 | 5.15 ± .22 | 5.25 ± .46 | 6.95 ± .44 |
| Day 2 | 4.84 ± .38 | 4.58 ± .23 (73) | 3.65 ± .29 (71) | 4.02 ± .47 (77) | 4.20 ± .28 (60) |
| Day 3 | 5.02 ± .36 | 3.82 ± .31 (61) | 3.35 ± .09 (65) | 3.18 ± .25 (61) | 3.65 ± .20 (53) |
| Day 4 | 5.12 ± .36 | 3.95 ± .29 (63) | 3.50 ± .20 (68) | 3.32 ± .17 (63) | 3.42 ± .29 (49) |
| Day 5 | 4.90 ± .35 | 4.05 ± .33 (64) | 3.12 ± .06 (61) | 3.08 ± .12 (59) | 3.25 ± .21 (47) |
| Day 6 | 4.89 ± .29 | 4.02 ± .35 | 3.42 ± .06 | 3.30 ± .18 | 3.22 ± .18 |

TABLE I-continued

| SERUM URIC ACID CONCENTRATION (MEAN MG/DL ± S.E.) | | | | |
|---|---|---|---|---|
| Placebo | Treatment | | | |
| | 200 mg | 300 mg | 400 mg | 500 mg |
| | (64) | (66) | (63) | (46) |

The numbers in parenthesis indicate the percentage of the pretreatment value for the respective treatments. From the table it can be seen that, in all instances, a clear reduction of serum uric acid concentration was observed.

In another study, six patients with hyperuricemia received multiple-dose medication in the following order: (1) 3 days of placebo; (2) 3 days of the sodium salt of 3-(1H-tetrazol-5-yl)-4(3H)-quinazolinone; and (3) 3 days of placebo. The active ingredient was administered orally 4 times daily on the indicated days in the form of tablets with each tablet containing 500 mg of active ingredient. Serum uric acid and urinary uric acid and creatinine were measured. The results observed are summarized in Table II.

factor in the reduction of serum uric acid levels observed.

What is claimed is:

1. A method of reducing the level of uric acid in the blood which comprises administering orally, to a human in which a reduction of the level or uric acid in the blood is desired, and effective amount, for reducing the level of uric acid in the blood, of 3-(1H-tetrazol-5-yl)-4(3H)-quinazolinone or a pharmaceutically acceptable salt thereof.

2. A method of treating hyperuricemia which comprises administering orally to a human hyperuricemic patient an effective amount, for treating hyperuricemia, of 3-(1H-tetrazol-5-yl) -4(3H)-quinazolinone or a pharmaceutically acceptable salt thereof.

TABLE II

| PLACEBO PRETREATMENT DAYS | | | TREATMENT DAYS | | | PLACEBO POST-TREATMENT DAYS | | |
|---|---|---|---|---|---|---|---|---|
| 1 | 2 | 3 | 1 | 2 | 3 | 1 | 2 | 3 |
| Serum Uric Acid (mg/dl) | | | | | | | | |
| 8.5 ± .2 | 8.5 ± .2 | 8.5 ± .2 | 6.0* ± .3 | 4.8* ± .3 | 4.4* ± .3 | 5.6* ± .3 | 7.1* ± .4 | 7.8 ± .4 |
| Urinary Uric Acid (mg/24 hr) | | | | | | | | |
| 448 ± 27 | 376 ± 41 | 392 ± 50 | 668* ± 88 | 559 ± 104 | 511 ± 81 | 400 ± 64 | 363 ± 35 | 436 ± 53 |
| Urate Clearance (ml/min) | | | | | | | | |
| 3.3 ± .1 | 2.7 ± .2 | 2.8 ± .2 | 6.9* ± 1.0 | 7.4* ± 1.4 | 7.2* ± 1.0 | 4.3 ± .5 | 3.2 ± .3 | 3.4 ± .3 |
| Creatinine Clearance (ml/min) | | | | | | | | |
| 86.4 ± 13.6 | 84.9 ± 13.6 | 79.3 ± 11.5 | 76.3 ± 11.7 | 76.0 ± 10.0 | 72.4 ± 10.4 | 81.5 ± 10.8 | 79.9 ± 12.0 | 82.7 ± 11.3 |
| $C_{urate}/C_{creat} \times 100$ | | | | | | | | |
| 4.4 ± .8 | 3.4 ± .4 | 3.8 ± .4 | 9.8* ± 1.1 | 10.1* ± 1.9 | 9.9* ± .4 | 5.7 ± 1.0 | 4.6 ± .8 | 4.5 ± .6 |

*$p < 0.05$ Compared to Placebo Pretreatment Day 3

From the above table it can be seen that serum urate decreased significantly during treatment, but, by the third day of post-treatment placebo, serum urate concentrations reverted to the baseline level. Renal urate clearance also increased significantly during the treatment. From the above results, it would appear that serum levels of uric acid were lower because of increased excretion of uric acid rather than as a result of any inhibition of uric acid synthesis in the body. Nevertheless, there still may be some inhibition of uric acid synthesis in the body although this would be a minor 3. A method according to claim 2 which comprises administering an effective amount of the sodium salt of 3-(1H -tetrazol-5-yl)-4(3H)-quinazolinone.

4. A method according to claim 2 wherein the sodium salt of 3-(1H-tetrazol-5-yl)-4(3H)-quinazolinone is administered 4 times daily at a dose of from 50 to 500 mg for each administration.

5. A method according to claim 2 wherein the sodium salt of 3-(1H-tetrazol-5-yl)-4(3H)-quinazolinone is administered orally at a dose of 500 mg 4 times daily.

* * * * *

UNITED STATES PATENT AND TRADEMARK OFFICE
CERTIFICATE OF CORRECTION

PATENT NO. : 4,757,075

DATED : July 12, 1988

INVENTOR(S) : Steven R. Wagner

It is certified that error appears in the above-identified patent and that said Letters Patent are hereby corrected as shown below:

Column 4, line 13, "the level or uric acid" should read -- the level of uric acid --.

Column 4, line 14, "and effective amount," should read -- an effective amount, --.

Signed and Sealed this

Twenty-eighth Day of February, 1989

Attest:

DONALD J. QUIGG

Attesting Officer

Commissioner of Patents and Trademarks